United States Patent [19]
Nakazawa et al.

[11] Patent Number: 5,604,780
[45] Date of Patent: Feb. 18, 1997

[54] METHOD FOR PROCESSING A RADIATION IMAGE

[75] Inventors: Masayuki Nakazawa; Hideyuki Handa; Wataru Motoki, all of Hino, Japan

[73] Assignee: Konica Corporation, Tokyo, Japan

[21] Appl. No.: 397,798

[22] Filed: Mar. 3, 1995

[30]  Foreign Application Priority Data

Mar. 10, 1994 [JP] Japan ................................. 6-039844

[51] Int. Cl.⁶ .................................................. G01N 23/04
[52] U.S. Cl. ................................. 378/62; 364/413.13
[58] Field of Search ...................... 364/413.13, 413.23; 378/62, 87

[56]   References Cited

U.S. PATENT DOCUMENTS 4,315,318  2/1982  Kato et al. ........................... 382/264
4,317,179  2/1982  Kato et al. ........................... 382/264
4,747,052  5/1988  Hishinuma et al. ............... 364/413.13
4,941,190  7/1990  Joyce ..................................... 382/54

Primary Examiner—David P. Porta
Assistant Examiner—David Vernon Bruce
Attorney, Agent, or Firm—Frishauf, Holtz, Goodman, Langer & Chick

[57]   ABSTRACT

A method for processing a radiographic image to obtain a processed image signal Sproc based on an original image signal Sorg. The method including the steps of: obtaining the original image signal Sorg representing the radiographic image based on radiographic image information transmitted through an object; obtaining an unsharp mask signal Sus corresponding to the original image signal Sorg; and conducting an operation presented by the formula: Sproc= A(Sorg)+B(Sus). In the formula, A(Sorg) is the function which does not include the unsharp mask signal Sus, B(Sus) is the function which does not include the original image signal Sorg.

23 Claims, 6 Drawing Sheets

FIG. 5

| | | SPROC OPERATION | | | SUB CALCULATION | OPERATION CALCULATION | | ARTIFACT | |
|---|---|---|---|---|---|---|---|---|---|
| | | NUMBER OF TIMES OF ADDITION AND SUBTRACTION | NUMBER OF TIMES OF MULTIPLICATION | CAPACITY OF TABLE MEMORY (BYTE) | CALCULATION TIME (SEC) | CALCULATION TIME (SEC) | SUM TOTAL | k1 | k2 |
| COMPARATIVE EXAMPLE 1 | TABLE MAKING OPERATION OF EACH PIXEL | 0 | 0 | 0 | 0 | | | NO | NO |
| | TOTAL | 2×2048×2048 8,388,608 | 1×2048×2048 4,194,304 | — | 25 | 30 | 55 | | YES |
| COMPARATIVE EXAMPLE 2 | TABLE MAKING OPERATION OF EACH PIXEL | 2×4096×4096 | 1×4096×4096 | 2×4096 ×4096 | 72 | | | NO | NO |
| | TOTAL | 33,554,432 | 16,777,216 | 33,554,432 | 8 80 | 30 | 110 | | YES |
| EXAMPLE 1 | TABLE MAKING OPERATION OF EACH PIXEL | 1×4096 | 2×4096 | 2×4096×2 | NOT MORE THAN 0.1 | | | NO | NO |
| | TOTAL | 1×2048×2048 4,198,400 | 8,192 | 16,384 | 10 | 30 | 40 | | YES |
| EXAMPLE 2 | TABLE MAKING OPERATION OF EACH PIXEL | 1×4096 | 2×4096 | 2×4096×2 | NOT MORE THAN 0.1 | | | NO | NO |
| | TOTAL | 1×2048×2048 4,198,400 | 8,192 | 16,384 | 10 | 30 | 40 | | NO |
| EXAMPLE 3 | TABLE MAKING OPERATION OF EACH PIXEL | 1×4096 | 2×4096 | 2×4096×2 | NOT MORE THAN 0.1 | | | NO | NO |
| | TOTAL | 1×2048×2048 4,198,400 | 8,192 | 16,384 | 10 | 15 | 25 | | YES |
| EXAMPLE 4 | TABLE MAKING OPERATION OF EACH PIXEL | 1×4096 | 2×4096 | 4096×2 +61504×2 | NOT MORE THAN 0.1 | | | NO | NO |
| | TOTAL | 1×2048×2048 4,198,400 | 8,192 | 65,600 | 10 | 15 | 25 | | YES |

METHOD FOR PROCESSING A RADIATION IMAGE

FIELD OF THE INVENTION

The present invention relates to a method for processing a radiation image, and more particularly relates to a method for processing a radiation image in a radiographic system used for medical diagnosis.

BACKGROUND

Conventionally, the following radiographic system is known:

After radioactive rays have been transmitted through a photographic object, they are absorbed by a fluorescent substance, so that the radioactive ray image information is recorded in the fluorescent substance. Then the fluorescent substance is scanned and excited with laser rays, and light is emitted from the fluorescent substance. This emitted light is detected by a photo detector. Light beams are modulated by this detected radioactive ray image information, and the radioactive ray image is recorded on a recording medium such as a photographic film.

Compared with a conventional silver salt type radioactive ray photographic system, the above radioactive ray photographic system in which the fluorescent substance is used has a wide latitude of radioactive ray exposure so as to record an image. From this point of view, the above radioactive ray photographic system has a very high utility value. The above radioactive ray photographic system is effectively applied to an X-ray photographic system for photographing human bodies.

X-rays are harmful to human bodies when the exposure dosage is increased. Therefore, it is desirable to make an amount of information provided by one photographing operation as large as possible. However, X-ray photographic films to be used at present must have not only an aptitude for photographing but also an aptitude for observation. Therefore, the X-ray photographic films to be used at present have both aptitudes to some extent. For this reason, concerning the aptitude for photographing, the X-ray exposure latitude is not sufficiently wide, and concerning the aptitude for observation, the image quality is not sufficiently high for medical diagnosis.

In order to solve the above problems, the following method for processing radioactive ray images are disclosed:

(1) Japanese Patent Publication No. 62373/1987 (Conventional Example 1)

This method is described below:
A fluorescent substance is scanned with rays of exciting light, so that radioactive ray image information recorded in the fluorescent substance is read out. After the image information has been converted into electric signals, it is reproduced on a recording medium in the following manner. An unsharp mask signal Sus corresponding to an extremely low frequency is found at each scanning point. Operation is carried out in accordance with the following expression.

$$S'=Sorg+\beta(Sorg-Sus) \qquad (1)$$

where Sorg is an original image signal that has been read from the fluorescent substance, $\beta$ is an emphasis coefficient, and S' is a reproduction image signal. In this way, frequency components not lower than the above extremely low frequency are emphasized.

In the above expression, the unsharp mask signal Sus corresponding to the extremely low frequency is defined as a signal in which the original image is blurred so that the original image only contains low frequency components lower than the extremely low frequency component. In this method, the emphasis coefficient $\beta$ is simply increased in accordance with an increase of the original image signal Sorg or the unsharp mask signal Sus. Further, in this method, the unsharp mask signal Sus is found when the original image signals Sorg are simply averaged in the mask.

According to this method, the frequency components not lower than the extremely low frequency which are effective for medical diagnosis are emphasized so that the contrast can be enhanced. In this way, the medical diagnosis performance can be improved.

(2) Japanese Patent Publication No. 62383/1987 (Conventional Example 2)

This method is described below:
An accumulation type fluorescent substance is scanned with rays, so that radioactive ray image information recorded in the fluorescent substance is read out. After the image information has been converted into electric signals, it is reproduced as a visual image on a recording medium in the following manner. An unsharp mask signal Sus corresponding to an extremely low frequency is found at each scanning point. Operation is carried out in accordance with the following expression.

$$S'=Sorg+F(X) \qquad (2)$$

(In this case, X and F(X) are expressed as follows.

X=Sorg−Sus.

F(X) is described below.

When $|X1|<|X2|$, the inequalities $F'(X1) \geq F'$ and $(X2) \geq 0$ are satisfied. With respect to X0 that satisfies $|X1|<|X0|<|X2|$, F(X) is a monotone increasing function that satisfies the inequality $F'(X1) > F'(X2)$.

where Sorg is an original image signal that has been read from the fluorescent substance, and S' is a reproduction image signal. In this way, frequency components not lower than the above extremely low frequency are emphasized.

In this case, values of F(X) can be stored in the form of a table.

There is a tendency that an artifact is generated in a region where the difference signal |Sorg−Sus| is high. From the viewpoint described above, according to this method, the frequency is more emphasized in a portion where the difference signal |Sorg−Sus| is high. Accordingly, it is possible to carry out image processing in which the generation of an artifact is suppressed.

According to the former conventional method described above, it requires a long period of time to carry out an operation. In order to reduce the operation time, it is suggested to employ a table-looking system in which the operation values are previously stored in the form of a table. However, when a ratio of emphasis of frequency, which is the emphasis coefficient $\beta$ in the conventional example 1, is changed in accordance with an increase of Sorg or Sus, the following problems may be encountered.

When the emphasis coefficient $\beta$ is a function which changes in accordance with a change in Sorg (in this case, the function is expressed by $\beta$ (Sorg)), the expression of the conventional example 1 can be transformed as follows.

$$S' = Sorg + \beta(Sorg)(Sorg - Sus) \quad (3)$$
$$= (1 + \beta(Sorg)) \cdot Sorg - \beta(Sorg) \cdot Sus$$
$$= F(Sorg) + G(Sorg, Sus)$$

In this case, $F(Sorg) = (1+\beta(Sorg)) \cdot Sorg$ $G(Sorg, Sus) = -\beta(Sorg) \cdot Sus$ (F is a function of Sorg, and G is a function of Sorg and Sus.)

When the emphasis coefficient $\beta$ is a function which changes in accordance with a change in Sus (in this case, the function is expressed by $\beta(Sus)$), the expression of the conventional example 1 can be transformed as follows.

$$S' = Sorg + \beta(Sus)(Sorg - Sus) \quad (4)$$
$$= (1 + \beta(Sus)) \cdot Sorg - \beta(Sus) \cdot Sus$$
$$= P(Sorg, Sus) + Q(Sus)$$

In this case, $P(Sorg, Sus) = (1+\beta(Sus)) \cdot Sorg$ $Q(Sus) = -\beta(Sus) \cdot Sus$ (F is a function of Sorg and Sus, and G is a function of Sus.)

In any cases, terms of both Sorg and Sus are included. Accordingly, when the values are stored in the table-looking system, it is necessary to provide a two-dimensional arrangement. Therefore, a large capacity of memory is required for storing the table.

In some cases, it is preferable that the table is calculated or transformed for each image. In this case, however, it takes a long period of time for table calculation. Therefore, it is not possible to reduce the operation time. Further, when $\beta$ is sharply changed, an artifact is generated, which may cause a wrong diagnosis. Further, when Sus is found by calculating a simple average of the signals in the mask, it is necessary to conduct a division, so that it takes a long period of time for operation.

In the latter conventional system described above, a table is required, the dimensions of which are (a range of values of Sorg + a range of values of Sus). Not only the addition and subtraction of each term but also the operation of the argument X (=Sorg–Sus) is required for each pixel. Therefore, it is difficult to shorten the operation time sufficiently. In order to omit the calculation of the argument X, X may be a function of Sorg and Sus like f (Sorg, Sus). In this case, however, a large capacity of table memory is required. Further, there is a description that f(X) may include a function of Sorg and/or Sus. In this case, a large capacity of table memory is also required in the same manner as that of the conventional technique (1) described before. In the description, there is provided no concept that the operation speed is increased when the function of only one of Sorg and Sus is added or subtracted.

SUMMARY OF THE INVENTION

In view of the problems described above, the present invention has been accomplished. It is an object of the present invention to provide a method for processing a radiation image in which the operation speed is increased and the memory capacity is reduced.

The present invention provides a method for processing a radiation image by which an original image signal "Sorg" to express an original image based on a radiation image transmitted through a photographic object is processed and a processed image signal "Sproc" having a frequency characteristic different from that of the original image is found.

One example of the present invention is characterized in that the processing is carried out in accordance with the following expression.

$$Sproc = A(Sorg) + B(Sus) \quad (5)$$

where Sus: Unsharp signal

A(Sorg): Function of Sorg excluding Sus

B(Sus): Function of Sus excluding Sorg

The other example of the present invention is described as follows. The present invention is to provide a method for processing a radiation image by which an original image signal "Sorg" based on the radiation image information transmitted through a photographic object is processed using an unsharp signal Sus and a processed image signal "Sproc" having a frequency characteristic different from that of the original image is found. In this case, the aforementioned Sus is found when the total Stotal of the original image signals Sorg of pixels, the number of which is N, in a predetermined mask including the objective pixels is shifted to the right by z bits (z is a positive integer), that is, when the total Stotal of the original image signals Sorg of pixels is shifted in the direction of LSB (Least Significant Bit).

For example, as the value of Stotal is expressed as "1010" in a binary code, the value of Stotal becomes "0101" when it is shifted one bit to the direction of LSB.

In the present invention, the processed image signal Sproc is expressed in the form of addition of A(Sorg) and B(Sus). According to this expression, A(Sorg) and B(Sus) are respectively independent functions of Sorg (original image) and Sus (unsharp image). The expression does not include a term composed of both Sorg and Sus. Therefore, the operation speed is increased. Even when A(Sorg) and B(Sus) are respectively stored in the form of a table, the memory capacity is not so large.

Also, the sharp signal Sus is found when the Stotal, which is the total of the original image signals Sorg of N pixels in a predetermined mask area including the target pixel, is shifted to the right by z bits (z is a positive integer). Due to the foregoing, the processing is not carried out by the operation of Stotal/N, but the processing is carried out by the right shift operation. Accordingly, the processing speed can be greatly increased.

BRIEF DESCRIPTION OF THE DRAWINGS

FIG. 5 is a table for the comparison of the operation time of a conventional example and the operation time of the present invention.

DETAILED DESCRIPTION OF THE INVENTION

With reference to the accompanying drawings, an example of the present invention will be explained in detail as follows.

Figure 1:
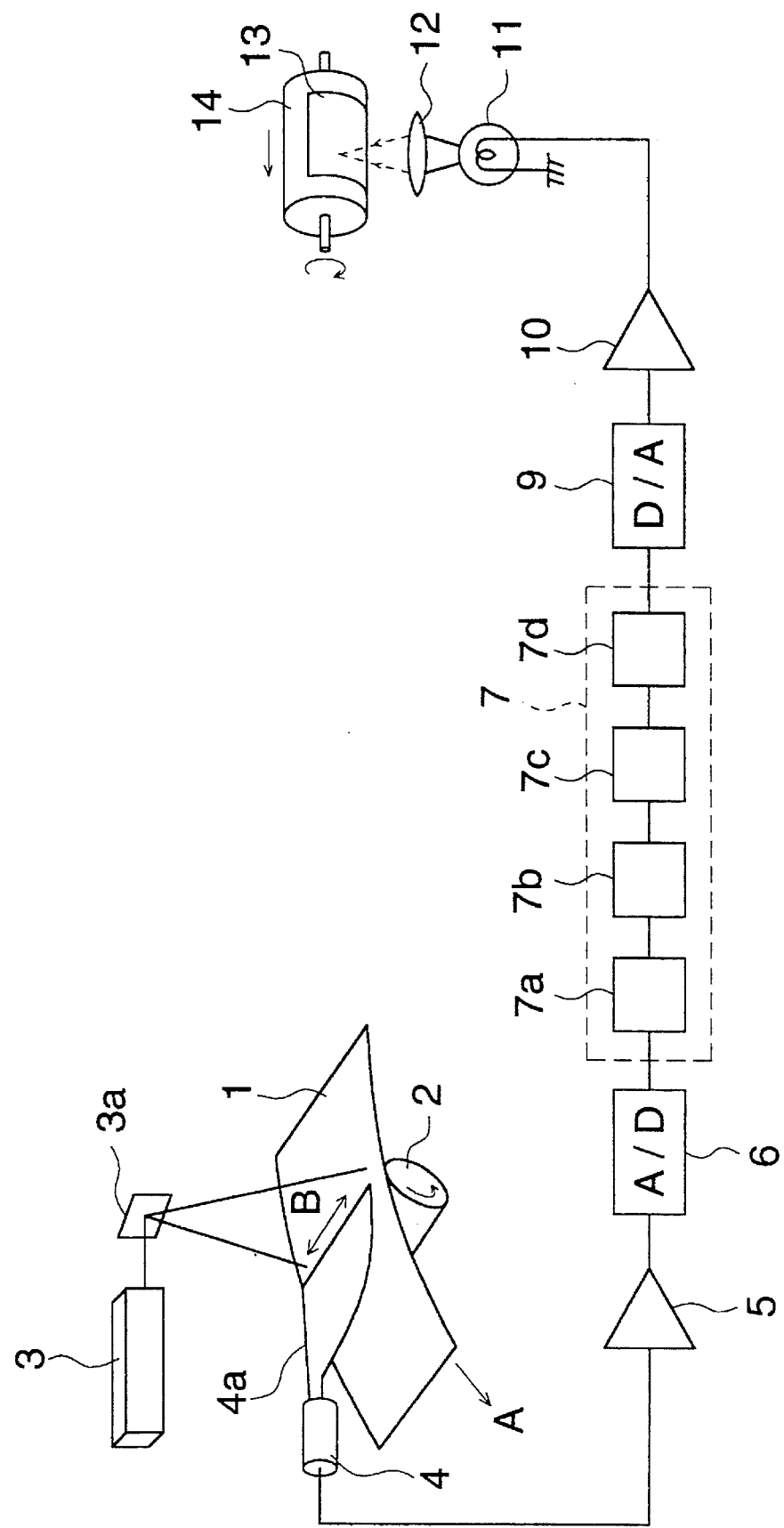
FIG. 1 is a block diagram showing an example of system structure for realizing the method of the present invention.

FIG. 1 is a block diagram showing an example of system structure for realizing the method of the present invention. When X-rays are applied to human's body, X-rays are transmitted through the body and incident upon a fluorescent material board. On this fluorescent material board, energy of the X-ray image is accumulated to the trap level of the fluorescent material. Due to the X-ray photography described above, the radiation image is accumulated and recorded on an accumulation type fluorescent sheet 1. The accumulation type fluorescent sheet 1 is conveyed by a roller 2. The sheet 1 is conveyed by the roller 2 in the direction of arrow A, and the subsidiary scanning is conducted on the sheet 1 so as to read the image on the sheet.

The primary scanning is conducted when the laser beams emitted by a laser beam source 3, the wavelength of excitation light of which is 500 to 800 nm, are subjected to scanning operation by a scanning mirror 3a in the direction of arrow B. By the scanning of the excitation light, photo stimulated luminescence light is generated, the wavelength range of which is 300 to 500 nm. This photo stimulated luminescence light is detected and converted into an electric signal by a photo detector 4 such as a photo multiplier arranged at the output end of the light collecting body 4a composed of light-conductive sheets. This electric signal is amplified by an amplifier 5 and converted into a digital signal by an A/D converter 6. Then the digital signal is sent to an operation section 7.

In the operation section 7, unsharp mask signal Sus is found by a calculating element 7a, function B(Sus) is found by a calculating element 7b, function A(Sorg) is found by a calculating element 7c, and Sproc=A(Sorg)+B(Sus) is found by a calculating element 7d. The thus provided digital signal Sproc is converted into an analog signal by the D/A converter 9 and amplified by the amplifier 10. Then the amplified signal is inputted into a light source 11 for recording.

Light is emitted from the light source 11 for recording. Then light passes through the lens. After that, light is irradiated on a recording material such as a photographic film attached onto the printing drum 14. The radiation image is reproduced on this photographic film, and the reproduced image is used for q medical diagnosis.

The present invention is to provide an image processing method employed in the calculating section 7. Therefore, it should be noted that the present invention is not limited to the specific image input method and image display method described above. For example, the following image input method may be adopted:

A photographic film is irradiated with a beam of light. The reflected beam of light or a transmitted beam of light is optically read so as to obtain a digital image signal. Concerning image display method, instead of printing an image on a photographic film, it may be displayed on a CRT.

Operation of the calculating section 7 will be explained as follows. In the present invention, Sproc is found by the following expression.

$$Sproc=A(Sorg)+B(Sus) \quad (5)$$

where Sus: Unsharp signal

A(Sorg): Function of Sorg excluding Sus

B(Sus): Function of Sus excluding Sorg

When the unsharp signal Sus is a simple average of the original image signals in a predetermined mask including the objective pixels, the calculating time can be preferably shortened. However, the weighted average, median and mode may be used instead of the simple average. Configuration of the mask may be rectangular, circular, cross, X-shaped and annular. Further, these various configurations may be combined. When data is processed by a computer, it is preferable that the mask configuration is rectangular, and it is most preferable that the mask configuration is square.

In the case where the unsharp signal Sus is found, signals of all pixels in the mask may be used. Alternatively, sampling may be carried out at regular intervals and signals of some of the pixels may be used. When at least one of functions A(Sorg) and B(Sus) is previously stored in the form of a table, it is not necessary to carry out the operation for each pixel each time. Accordingly, the calculating time is preferably reduced. The composition of the photographic object is different for each part, and even when the part is the same, the composition is different for each photographic object. Therefore, when a table is made for each image in accordance with the characteristic amount of an image such as a maximum value, minimum value, average and frequency characteristics in the most concerned region, the image can be most appropriately processed, and the image quality can be enhanced.

When the reference table is rotated and moved in parallel in accordance with the characteristic amount of an image, the reference table is varied. When the varied table is used, a complicated function, which is not expressed by a simple expression, can be simply made for each image. Therefore, it is preferable that the reference table is rotated and moved in parallel in accordance with the characteristic amount of an image to find the varied table. Alternatively, a different reference table may be stored for each part, and the reference table is selected in accordance with the photographed part information. Further, the reference table may be varied for each image in accordance with the characteristic amount and the radioactive ray condition.

It is preferable that A(Sorg) is at least the product of function a(Sorg), which changes in accordance with a change in Sorg, and Sorg. It is also preferable that B(Sus) is at least the product of function b(Sus), which changes in accordance with a change in Sus, and Sus.

It is preferable that a(Sorg) and b(Sus) are expressed by the following expressions.

$$a(Sorg)=(1+k(Sorg))$$

$$b(Sus)=-k(Sus) \quad (6)$$

As a result, the processed image signal Sproc is expressed by the following expression.

$$Sproc = (1 + k(Sorg)) \cdot Sorg \quad (7)$$
$$= +(-k(Sus)) \cdot Sus$$

In the case where A(Sorg) and B(Sus) are sharply changed, a mock image appears. At this time, when A(Sorg) is the product of function a(Sorg), which changes in accordance with a change in Sorg, and Sorg, and also when B(Sus) is the product of function b(Sus), which changes in accordance with a change in Sus, and Sus, the conversion table is made using the following expressions.

$$A(Sorg) = \int_0^{Sorg} a(s) \cdot ds \text{ or } A(Sorg) = \sum_{S=0}^{Sorg} a(s) \cdot \Delta s$$

$$B(Sus) = \int_0^{Sus} b(s) \cdot ds \text{ or } B(Sus) = \sum_{S=0}^{Sorg} b(s) \cdot \Delta s$$

In the above calculating expressions, a(S) or b(S) is accumulated from 0 to Sorg, or from 0 to Sus. Due to the foregoing, a change in the value on the correction table becomes gentle, so that the occurrence of a mock image can be prevented and the image quality can be improved.

This point will be explained in further detail.

The calculating expression of the frequency emphasizing processing of the conventional example described above can be deformed as follows.

$$Qprc = Qorg + k(Qus) \cdot (Qorg - Qus) \qquad (8)$$
$$= \{1 + k(Qus)\} \cdot Qorg - k(Qus) \cdot Qus$$

In the above expression, the first term includes a mutual operation of Qus and Qorg. Therefore, it takes time for operation. For this reason, it is desirable to realize a calculating expression in which the first and second terms do not include a mutual operation of Qus and Qorg and further the image quality is not deteriorated. For example, when the first term of the calculating expression is a function of only Qorg and the second term of the calculating expression is a function of only Qus, LUT processing can be independently carried out in parallel, so that the calculating time can be shortened. That is, k(Qus) in the above expression may be replaced with k(Qorg). In other words, k(Qus) in the above expression may be approximated to k(Qorg). Then the following operation may be carried out.

$$Qproc = \{1+k(Qorg)\} \cdot Qorg - k(Qus) \cdot Qus \qquad (9)$$

Figure 2:
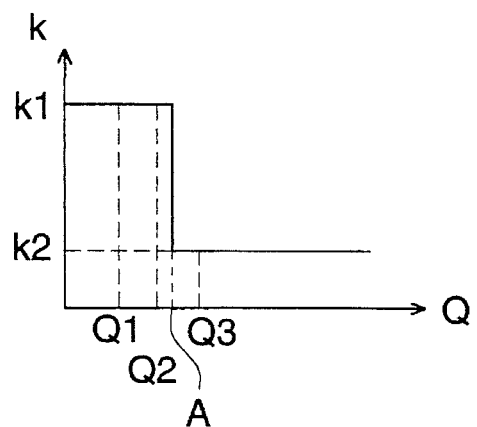
FIGS. 2(a) to 2(c) are schematic illustrations for explaining the approximation of expressions.
Figure 2:
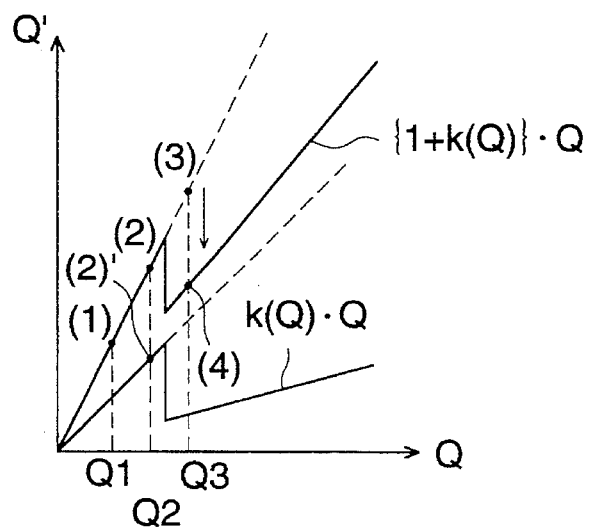
Figure 2:
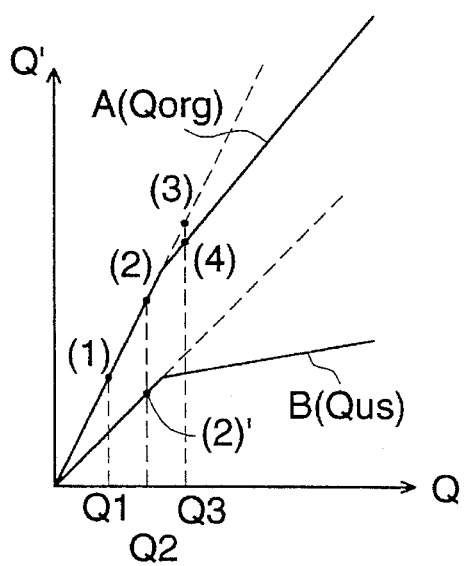
Figure 3:
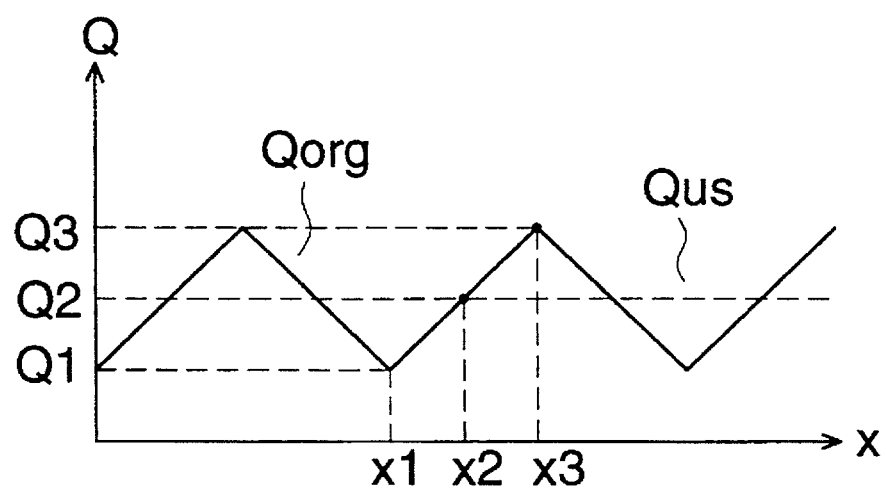
FIG. 3 is a graph showing an example of the signal waveforms of Qorg and Qus.

When the emphasizing coefficient k is gradually changed, no problems are caused. However, when the emphasizing coefficient k is changed stepwise as shown in FIG. 2(a), there is a possibility of generation of a mock image. The signal shown in FIG. 3 is taken as an example and explained below. As illustrated in FIG. 3, Qorg changes like triangular waves, however, Qus is an average value, so that it is constant. The values of Qorg at the points x1, x2 and x3 are respectively Q1, Q2 and Q3, and Qus is Q2. FIG. 2(b) shows the first term $\{1+k(Qorg)\} \cdot Qorg$ and the second term $k(Qus) \cdot Qus$. The second term is always (2)' at the points x1, x2 and x3. In the case of the expression (8), the first terms are respectively (1), (2) and (3) with respect to Q1, Q2 and Q3. In the case of the expression (9), the first term with respect to Q3 is (4), which is larger than (2) with respect to Q2. Accordingly, when the operation processing is carried out onlyby the expression (9), there is a possibility of generation of a mock image.

In order to prevent the occurrence of a mock image, a method may be employed in which the following expression is deformed. This method is based on the concept described below:

Expression (6) is a linear expression of Qorg and Qus, and $\{1+k(Qorg)\}$ and Q(Qus) are differential coefficients of the linear expression. When the differential coefficient is integrated by Qorg (or Qus), the original function is obtained.

$$Qorg = A(Qorg) - B(Qus) \qquad (10)$$

where

A(Qorg): Accumulation function of $1+k(Q)$

B(Qus): Accumulation function of $k(Q)$

According to this method, both A(Q) and B(Q) are continuous functions, so that a difference between (3) and (4) is small, and the first term is not reversed (shown in FIG. 2(c)). Accordingly, it is possible to prevent the generation of a mock image.

Next, the calculation method of the unsharp signal Sus will be explained as follows. When Sus is found by a simple average of Sorg, the correct method is described as follows: The total of Stotal of the original image signals Sorg of pixels, the number of which is N, in a predetermined mask including the objective pixel is divided by N so as to find Stotal/N. However, this method is disadvantageous in that the capacity of hardware used for operation is increased, and further an amount of software processing is increased. Accordingly, instead of dividing Stotal by N, Stotal is divided by $2^z$. That is, the operation is made in such a manner Stotal/$2^z$ This division is simple. The division is made in such a manner that Stotal is shifted to the right by z bits, wherein z is a positive integer. However, an error of $2^z/N$ is generated between N and $2^z$. Therefore, Sus is found in such a manner that the total Stotal of the original image signals Sorg of pixels, the number of which is N, in a predetermined mask including the objective pixel is shifted to the right by z bits. When $\alpha = 2^z/N$, operation is made in accordance with the following expression.

$$Sproc = A(Sorg, \alpha \cdot Sus) \qquad (11)$$

In this case, the operation is made when the function of Sproc is corrected by $\alpha$ times in the direction of Sus axis. In this way, it is not necessary to conduct a division, so that the operation time can be reduced. Especially when the calculating expression is stored in the form of a table, the operation time can be greatly reduced. Therefore, it is preferable to store the calculating expression in the form of a table.

Figure 4:
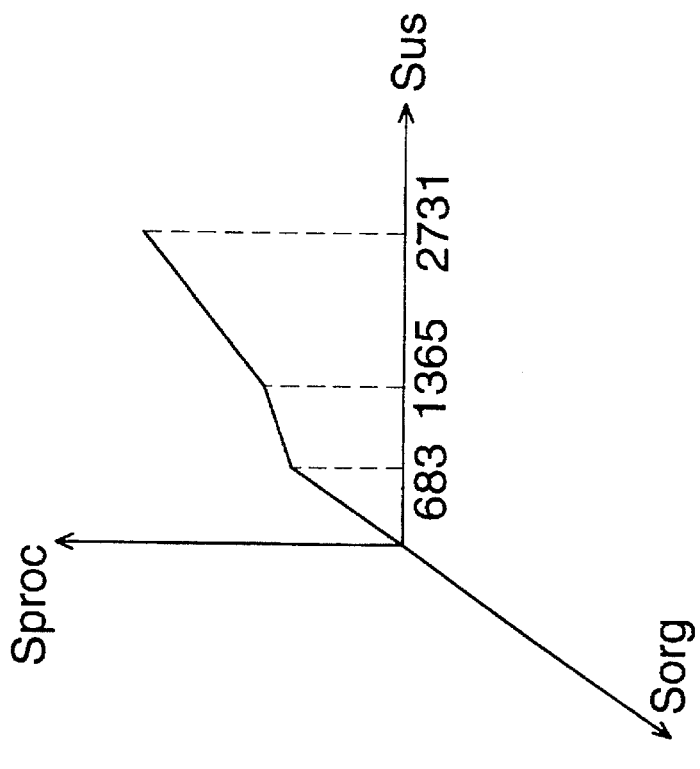
FIGS. 4(a) and 4(b) are schematic illustrations for explaining the correction of $\alpha$ times in the axial direction of Sus.
Figure 4:
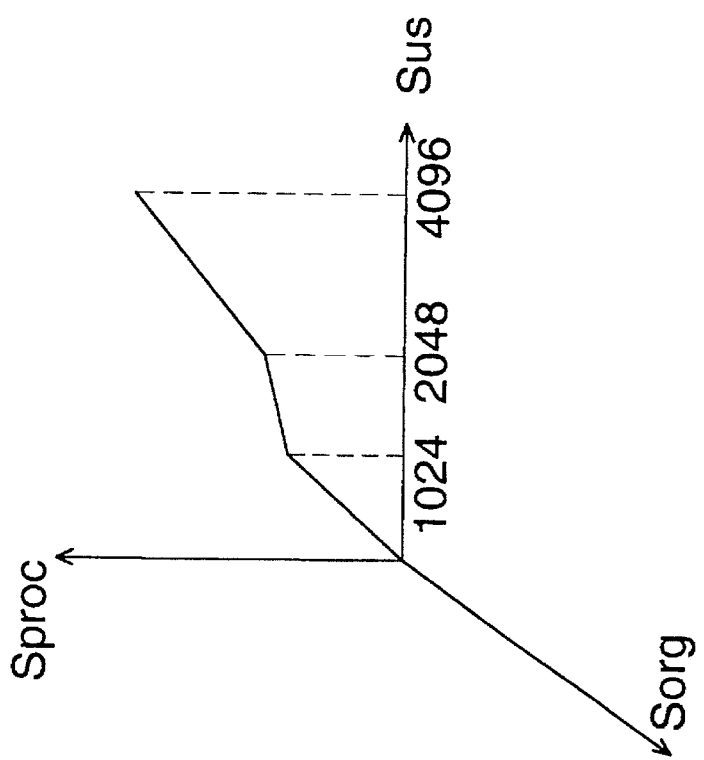

The matter described above will be explained in detail referring to FIGS. 4(a) and 4(b). When A'(Sorg, Sus)= A(Sorg, $\alpha$Sus) is used instead of A(Sorg, Sus), a function to find Sproc is corrected by $\alpha$ times on the Sus axis. In order to simplify the explanation, a specific explanation will be made on a plane of Sproc-Sus. For example, in the case of Sproc=A(Sorg, Sus), as illustrated in FIG. 4(a), Sproc is expressed by a linear function which increases in accordance with an increase of Sus, and an inclination of the straight line is changed by Sus=1024,2048. In the case of Sproc=a(Sorg, $\alpha$·Sus), the inclination is changed when s=1024,2048. Consequently, the function of A'(Sorg, Sus) is expressed in the form of a graph in such a manner that the function is reduced by $1/\alpha$ in the direction of Sus axis. In the case of $\alpha < 1$, the function is extendedby $1/\alpha$ in the direction of Sus axis.

Further, when Sus, obtainedby shifting the value of Stotal for z bits to the direction of LSB as described above, is in the range that Sus is used without multiplying by the correction value $\alpha$, the operation can be carried out according to the function expressed by Sproc=A(Sorg, Sus).

Next, an improvement of operation accuracy to find Sus will be explained as follows. Sus described above is found in the following manner:

The total Stotal of the original image signals Sorg of pixels, the number of which is N, in a predetermined mask including the objective pixel is shifted to the right by z bits. In this case, x is a minimum integer satisfying the inequality N $\leq 2^{z+P-q}$ the unsharp mask signal Sus is expressed by p bit of the gray scale level, and the original image signal Sorg is expressed by q bit of the gray scale level. When $\alpha = 2^z/N$, operation is made in accordance with the expression of Sporc=A(Sorg, $\alpha$·Sus). In this way, Sus can be expressed in a range of the bit number p in a desired gray scale level. When p is made to be larger than q, the occurrence of an error can be suppressed when the data is arranged in the form of a table. The larger the value of p–q is, the higher the operation accuracy is improved. However, when the operation accuracy is enhanced, the memory capacity of the table is increased. Therefore, from the viewpoint of practical use, the value of p–q preferably satisfies the inequality of $2 \leq p - q \leq 6$.

Next, the effect of the present invention will be explained in detail. FIG. 5 is a table for explaining the effect of the present invention. In the table, the effect of the present invention is compared with the effect of comparative examples. In FIG. 5, the operation time of the conventional example 1 and the operation time of the example of the present invention are compared. FIGS. 6(a) to 6(f) are graphs showing various functions used in the operation.

[COMPARATIVE EXAMPLE 1]

Image data was subjected to software processing in a general-use work station. With respect to Sorg, Sus and Sproc, image data was provided as follows:

2048 pixels×2048 pixels×density resolution 12 bits (4096 gradation)

Sus was found when the total Stotal of Sorg in the mask of 31×31 pixels was divided by the number 31×31 of pixels. The expression used for the operation was the same as that of the example of the prior art, which will be described below.

$$Sporc = Sorg + k(Sus) \times (Sorg - Sus) \quad (12)$$
$$= (1 + k(Sus)) \times Sus - k(Sus) \times Sus \quad (13)$$

Operation was made for each pixel in accordance with the expression (1). Concerning the emphasis coefficient k, the following two values were adopted. One is k2 shown in FIG. 6(a), and the other is k1 shown in FIG. 6(b).

[COMPARATIVE EXAMPLE 2]

The following expression was used.

$$A(Sorg, Sus) = (1+k(Sus)) \times Sorg - k(Sus) \times Sus$$

In this case, A(Sorg, Sus) was previously found in the form of a table in which the input was determined to be 12 bits and the output was determined to be 12 bits. The processed image signal Sproc was found for each pixel using the following expression.

$$Sproc = A(Sorg, Sus)$$

Other points were the same as those of Comparative Example 1. fin this case, the table A was in a two-dimensional arrangement, the number of elements of which was 4096×4096.

[Example 1]

Image data was subjected to software processing in a general-use work station. With respect to Sorg, Sus and Sproc, image data was provided as follows:

2048 pixels×2048 pixels×density resolution 12 bits (4096 gradation)

Sus was found when the Sorg in the mask of 31×31 pixels was simply averaged. The following expression was used in the operation.

$$Sporc = (1+k(Sorg)) \times Sorg - k(Sus) \times Sus$$

where $A(Sorg) = (1+k(Sorg)) \times Sorg$ $B(Sus) = -k(Sus) \times Sus$

In this case, A(Sorg) and B(Sus) were previously found in the form of a table in which the input was determined to be 12 bits and the output was determined to be 12 bits. The processed image signal Sproc was found for each pixel using the following expression.

$$Sporc = A(Sorg) + B(Sus)$$

In this case, the tables A and B were in a one-dimensional arrangement, the number of elements of which was 4096. In this case, the function k(Sorg) was established in the following two manners. One is a function in which k1 is used, and the other is a function in which k2 is used.

[Example 2]

$$A(Sorg) = \sum_{S=0}^{Sorg} (1 + k(Sorg)) \times \Delta s$$

$$B(Sus) = \sum_{S=0}^{Sorg} -k(Sus) \times \Delta s$$

where Δs=1

A(Sorg) and B(Sus) were found by the above expressions, and other points were the same as those of Example 1.

[Example 3]

Figure 6:
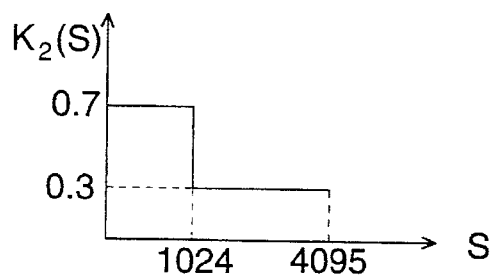
FIGS. 6(a) to 6(f) are graphs showing various functions used for the operation.
Figure 6:
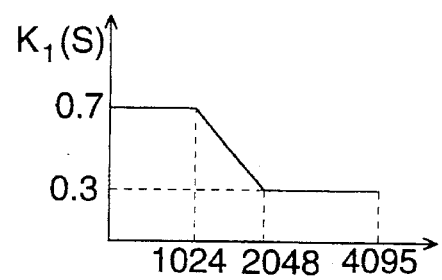
Figure 6:
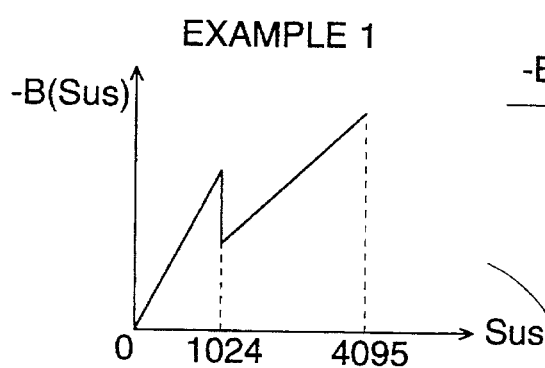
Figure 6:
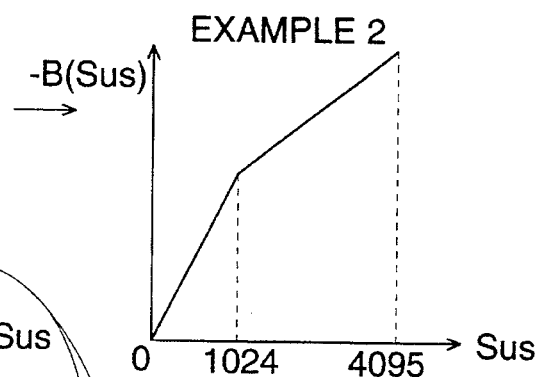
Figure 6:
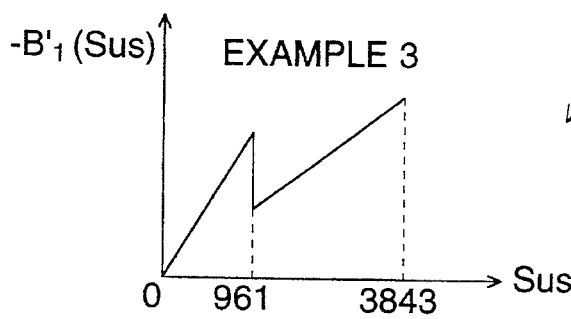
Figure 6:
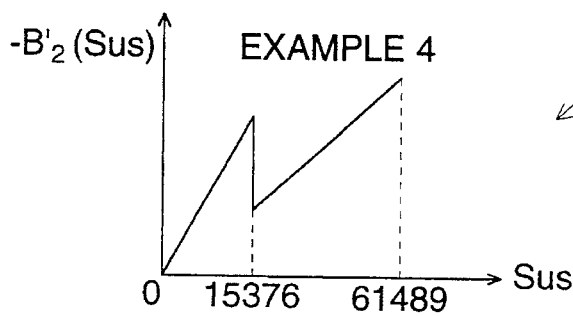

In this example, Sus was found in such a manner that the Stotal, which is the total of the Sorg in the mask of 31×31 pixels, was shifted to the right for 10 bits. Instead of B(Sus), the table B'(Sus) was used, the input of which was composed of 12 bits and the output of which was composed of 12 bits. Other points were the same as those of Example 2.

$$B'(Sus) = B(\alpha \cdot Sus) \quad (16)$$

where $\alpha = 2^{10}/31 \times 31$, and the configuration of B' is the same as that illustrated in FIG. 6(e).

[Example 4]

In this example, the number of bits of Sus in the dynamic range was 16, and Sus was found in such a manner that the Stotal, which is the total of Sorg in the mask of 31×31 pixels, was shifted to the right for 6 bits. Instead of B(Sus), the table B'(Sus) was used, the input of which was composed of 12 bits and the output of which was composed of 12 bits. Other points were the same as those of Example 2.

$$B'(Sus) = B(\alpha \cdot Sus) \quad (17)$$

where $\alpha = 2^6/31 \times 31$, and the configuration of B' is the same as that illustrated in FIG. 6(f).

In FIG. 5, the following are shown:

Number of addition and subtraction in the operation of Sproc, number of multiplication, capacity of memory necessary for the table, operation time, operation time of Sus, and existence of artifact. In Comparative Example 1, 30 seconds were required for the operation of Sus, and 25 seconds were required for the operation of Sproc, so that 55 seconds were required in total. In the case of k1 in which the function of k(Sus) is gently changed, the occurrence of artifact was avoided. In the case of k2 which was sharply changed, the occurrence of artifact was observed when the signal value was about 1024.

In Comparative Example 2, it took 72 seconds to calculate the table. Accordingly, the operation time of Comparative Example 2 was longer than that of Comparative Example 1. Further, the memory capacity of 32 M bytes was required for the table, which is not suitable for practical use.

In Example 1, the amounts of addition, subtraction and multiplication were greatly reduced. Therefore, the operation time of Sproc was reduced from 25 seconds to 10 seconds. The table operation time was not more than 0.1 second, which was negligibly small. Memory capacity necessary for the table was 16 K bytes, which caused no practical problems.

The operation time of Example 2 was the same as that of Example 1. Even when the function of k(Sus) was k2 which changed sharply, the occurrence of artifact was not observed and high image quality was provided.

Although the operation time of Sproc of Example 3 was the same as that of Example 1, the Sus operation time was reduced by 15 seconds. Therefore, the total operation time was 25 seconds, that is, the total operation time was reduced to a half of that of Comparative Example 1.

The operation time of Example 4 was the same as that of Example 3. Although it was not checked by the visual inspection, according to the analysis of signal values, it was found that the amount of quantization noise of Example 4 was larger than that of Example 1. The amount of quantization noise of Example 4 was smaller than that of Example 3.

As described above, according to the present invention, a calculating expression is used, in which the processed image signal Sproc is expressed in the form of a summation of the functions of one of the original image signal Sorg and the unsharp signal Sus. Accordingly, it is possible to provide a method for processing a radiation image by which the operation speed is increased and the memory capacity is reduced. Therefore, the present invention can provide a great practical effect.

When the rate of emphasis of frequency is changed in accordance with the increase of Sorg and/or Sus, the diagnosis ability can be enhanced and the operation time can be shortened. In the example of the present invention, the rate of emphasis of frequency is monotonously reduced in accordance with the increase of Sus or Sorg, that is, k(Sus) and k(Sorg) are monotonously reduced in accordance with the increase of Sus or Sorg. However, it should be noted that the rate of emphasis of frequency is not limited to the monotonous reduction. It is preferable that the monotone decreasing function, monotone increasing function and more complicated function are appropriately used in accordance with the part of an original image.

Even when the image processing method of the present invention is combined with other image processing methods such as gradation processing, the same effect can be provided. Therefore, it is preferable to combine the image processing method of the present invention with other image processing such as gradation processing. In this case, other image processing may be carried out before or after the image processing of the present invention.

What is claimed is:

1. A method for processing a radiographic image to obtain a processed image signal Sproc based on an original image signal Sorg, the method comprising the steps of:

obtaining the original image signal Sorg representing said radiographic image based on radiographic image information transmitted through an object;

obtaining an unsharp mask signal Sus corresponding to said original image signal Sorg; and conducting an operation presented by a formula (1):

$$Sproc = A(Sorg) + B(Sus) \quad (1)$$

wherein A(Sorg) is the function of said original image signal Sorg, which excludes said unsharp mask signal Sus, and B(Sus) is the function of said unsharp mask signal Sus, which excludes said original image signal Sorg.

2. The method of claim 1, wherein A(Sorg) includes the product of Sorg and a(Sorg) where a(Sorg) is the function which changes in correspondence with a change of Sorg; and B(Sus) includes the product of Sus and b(Sus) where b(Sus) is the function which changes in correspondence with a change of Sus.

3. The method of claim 2, wherein said A(Sorg) is the product of said Sorg and said a(Sorg), and B(Sus) is the product of said Sus and said b(Sus).

4. The method of claim 3, wherein said functions a(Sorg) and b(Sus) respectively satisfy formulas (2) and (3):

$$a(Sorg) = (1 + k(Sorg)) \quad (2)$$

$$b(Sus) = -k(Sus) \quad (3)$$

wherein k(Sorg) is the function which changes in correspondence with a change of Sorg; and k(Sus) is the function which changes in correspondence with a change of Sus.

5. The method of claim 1, wherein said operation conducting step includes the steps of:

referring to a conversion table, prestored in a memory, so as to obtain a conversion value corresponding to at least one of the functions A(Sorg) and B(Sus);

conducting a processing operation presented by said formula (1) in use with said conversion value for obtaining said processed image signal Sproc corresponding to one pixel of said radiographic image; and repeating said referring step of said conversion table and said processing operation conducting step in response to each pixel of said radiographic image so as to obtain said processed image signal Sproc.

6. The method of claim 5, wherein A(Sorg) includes the product of Sorg and a(Sorg) where a(Sorg) is the function which changes in correspondence with a change of Sorg; and B(Sus) includes the product of Sus and b(Sus) where b(Sus) is the function which changes in correspondence with a change of Sus.

7. The method of claim 6, wherein said A(Sorg) is the product of said Sorg and said a(Sorg), and B(Sus) is the product of said Sus and said b(Sus).

8. The method of claim 7, wherein said functions a(Sorg) and b(Sus) respectively satisfy formulas (2) and (3):

$$a(Sorg) = (1 + k(Sorg)) \quad (2)$$

$$b(Sus) = -k(Sus) \quad (3)$$

wherein k(Sorg) is the function which changes in correspondence with a change of Sorg; and k(Sus) is the function which changes in correspondence with a change of Sus.

9. The method of claim 5, wherein said operation conducting step further includes the steps of:

analyzing said radiographic image; and providing said conversion table, corresponding to said radiographic image, according to a result of said analyzing step.

10. The method of claim 9, wherein said conversion table is obtained by an operation presented by at least one of formulas (4) and (5):

$$A(Sorg) = \int_0^{Sorg} a(s) \cdot ds \text{ or } A(Sorg) = \sum_{S=0}^{Sorg} a(s) \cdot \Delta s \quad (4)$$

$$B(Sus) = \int_0^{Sus} b(s) \cdot ds \text{ or } B(Sus) = \sum_{S=0}^{Sus} b(s) \cdot \Delta s \quad (5)$$

wherein a(s) and b(s) are the functions which changes in correspondence with a change of s.

11. The method of claim 10, wherein said functions a(Sorg) and b(Sus) respectively satisfy formulas (2) and (3):

$$a(Sorg) = (1 + k(Sorg)) \quad (2)$$

$$b(Sus) = -k(Sus) \quad (3)$$

wherein k(Sorg) is the function which changes in correspondence with a change of Sorg; and k(Sus) is the function which changes in correspondence with a change of Sus.

12. The method of claim 5, wherein said conversion table is obtained by an operation presented by at least one of formulas (4) and (5):

$$A(Sorg) = \int_0^{Sorg} a(s) \cdot ds \text{ or } A(Sorg) = \sum_{S=0}^{Sorg} a(s) \cdot \Delta s \qquad (4)$$

$$B(Sus) = \int_0^{Sus} b(s) \cdot ds \text{ or } B(Sus) = \sum_{S=0}^{Sus} b(s) \cdot \Delta s \qquad (5)$$

wherein a(s) and b(s) are the functions which changes in correspondence with a change of s.

13. The method of claim 12, wherein said functions a(Sorg) and b(Sus) respectively satisfy formulas (2) and (3):

$$a(Sorg)=(1+k(Sorg)) \qquad (2)$$

$$b(Sus)=-k(Sus) \qquad (3)$$

wherein k(Sorg) is the function which changes in correspondence with a change of Sorg; and k(Sus) is the function which changes in correspondence with a change of Sus.

14. A method for processing a radiographic image to obtain a processed image signal Sproc of a target pixel based on an original image signal Sorg, the method comprising the steps of:

obtaining the original image signal Sorg representing said radiographic image based on radiographic image information transmitted through an object;

obtaining a signal Stotal which is a total of said original image signal Sorg corresponding to N pixels in a predetermined mask area including said target pixel, wherein N is an integer selected from both of the product of some powers of 2 and numbers other than the product of some powers of 2;

obtaining an unsharp mask signal Sus corresponding to said original image signal Sorg by shifting said signal Stotal in a direction of the Least Significant Bit for z bits; wherein z is a positive integer; and conducting an operation presented by a formula (6):

$$Sproc=A(Sorg, Sus) \qquad (6)$$

wherein said operation conducting step includes the steps of:

referring to a conversion table, prestored in a memory, so as to obtain a conversion value for a formula (7):

$$Sproc=A(Sorg, \alpha \cdot Sus) \qquad (7);$$

wherein α is a correction value;

conducting a processing operation presented by said formula (7) in use with said conversion value for obtaining said processed image signal Sproc corresponding to one pixel of said radiographic image; and repeating said referring step of said conversion table and said processing operation conducting step in response to each pixel of said radiographic image so as to obtain said processed image signal Sproc.

15. A method for processing a radiographic image to obtain a processed image signal Sproc of a target pixel based on an original image signal Sorg, the method comprising the steps of:

obtaining the original image signal Sorg representing said radiographic image based on radiographic image information transmitted through an object;

obtaining a signal Stotal which is a total of said original image signal Sorg corresponding to N pixels in a predetermined mask area including said target pixel; and obtaining an unsharp mask signal Sus corresponding to said original image signal Sorg by shifting said signal Stotal in a direction of the Least Significant Bit for z bits, wherein z is a positive integer;

conducting an operation presented by a formula (7):

$$Sproc=A(Sorg, \alpha \cdot Sus) \qquad (7);$$

wherein α is a conection value obtained by a formula (8):

$$\alpha=2^z/N \qquad (8).$$

16. The method of claim 15, wherein z is a minimum integer satisfying a formula (9):

$$N \leq 2^{z+p-q} \qquad (9)$$

said unsharp mask signal Sus is expressed by p bit of the gray scale level, and said original image signal Sorg is expressed by q bit of the gray scale level.

17. The method of claim 16, wherein variables p and q of said formula (9) satisfy a formula (10):

$$2 \leq p-q \leq 6 \qquad (10).$$

18. The method of claim 16, wherein said operation conducting step includes the steps of:

referring to a conversion table, prestored in a memory, so as to obtain a conversion value for said formula (7);

conducting a processing operation presented by said formula (7) in use with said conversion value for obtaining said processed image signal Sproc corresponding to one pixel of said radiographic image; and repeating said referring step of said conversion table and said processing operation conducting step in response to each pixel of said radiographic image so as to obtain said processed image signal Sproc.

19. The method of claim 17, wherein said operation conducting step includes the steps of:

referring to a conversion table, prestored in a memory, so as to obtain a conversion value for said formula (7);

conducting a processing operation presented by said formula (7) in use with said conversion value for obtaining said processed image signal Sproc corresponding to one pixel of said radiographic image; and repeating said referring step of said conversion table and said processing operation conducting step in response to each pixel of said radiographic image so as to obtain said processed image signal Sproc.

20. The method of claim 15, wherein said operation conducting step includes the steps of:

referring to a conversion table, prestored in a memory, so as to obtain a conversion value for said formula (7);

conducting a processing operation presented by said formula (7) in use with said conversion value for obtaining said processed image signal Sproc corresponding to one pixel of said radiographic image; and repeating said referring step of said conversion table and said processing operation conducting step in response to each pixel of said radiographic image so as to obtain said processed image signal Sproc.

21. A method for processing a radiographic image to obtain a processed image signal Sproc of a target pixel based on an original image signal Sorg, the method comprising the steps of:

obtaining the original image signal Sorg representing said radiographic image based on radiographic image information transmitted through an object;

obtaining a signal Stotal which is a total of said original image signal Sorg corresponding to N pixels in a predetermined mask area including said target pixel, wherein N is an integer selected from both of the product of some powers of 2 and numbers other than the product of some powers of 2;

obtaining an unsharp mask signal Sus corresponding to said original image signal Sorg by shifting said signal Stotal in a direction of the Least Significant Bit for z bits, wherein z is a positive integer; and conducting an operation presented by a formula (1):

$$Sproc = A(Sorg) + B(Sus) \tag{1}$$

wherein A(Sorg) is the function of said original image signal Sorg, which excludes said unsharp mask signal Sus, and B(Sus) is the function of said unsharp mask signal Sus, which excludes said original image signal Sorg.

22. The method of claim 21, wherein the function B(Sus) is a function of $\alpha \cdot Sus$, wherein $\alpha$ is a correction value.

23. The method of claim 22, wherein $\alpha$ is a correction value obtained by a formula (8):

$$\alpha = 2^z / N \tag{8}$$

* * * * *